(12) United States Patent
Edwards et al.

(10) Patent No.: US 7,146,978 B2
(45) Date of Patent: *Dec. 12, 2006

(54) INHALATION DEVICE AND METHOD

(75) Inventors: David Edwards, Boston, MA (US); Mark DeLong, Newton, MA (US); Craig Dunbar, Boston, MA (US); Ernest E. Penachio, Haverhill, MA (US); Kevin Stapleton, Seattle, WA (US); Mark Wolff, Somerville, MA (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/771,447

(22) Filed: Feb. 5, 2004

(65) Prior Publication Data

US 2004/0154618 A1  Aug. 12, 2004

Related U.S. Application Data

(62) Division of application No. 09/835,302, filed on Apr. 16, 2001, now Pat. No. 6,766,799.

(51) Int. Cl.
*A61M 16/00* (2006.01)
(52) U.S. Cl. ............................ 128/203.15; 128/203.21
(58) Field of Classification Search ........... 128/203.21, 128/203.15, 203.12; 604/58, 44, 94.01, 148, 604/520; 222/80, 81, 83.5, 85, 86, 88
See application file for complete search history.

(56) References Cited

U.S. PATENT DOCUMENTS

| | | |
|---|---|---|
| 3,635,219 A | 1/1972 | Altounyan et al. |
| 3,669,113 A | 6/1972 | Altounyan et al. |
| 3,795,244 A | 3/1974 | Lax et al. |
| 3,837,341 A | 9/1974 | Bell |
| 3,888,253 A | 6/1975 | Watt et al. |
| 3,906,950 A | 9/1975 | Cocozza |
| 4,013,075 A | 3/1977 | Cocozza |
| 4,069,819 A | 1/1978 | Valentini et al. |
| 4,105,027 A | 8/1978 | Lundquist |
| 4,192,309 A | 3/1980 | Poulsen |
| 4,240,418 A | 12/1980 | Rosskamp et al. |
| 4,338,931 A * | 7/1982 | Cavazza ............... 128/203.15 |
| 4,841,964 A | 6/1989 | Hurka et al. |
| 4,846,168 A | 7/1989 | Abiko et al. |

(Continued)

FOREIGN PATENT DOCUMENTS

WO    WO 94/08552 A2    4/1994

(Continued)

OTHER PUBLICATIONS

Bisgaard, H. et al., Fine particle mass from the Diskus inhaler and Turbuhaler inhaler in children with asthma, European Respiratory Journal, 11: 1111-1115, May 1998.

(Continued)

*Primary Examiner*—Henry Bennett
*Assistant Examiner*—Amadeus Lopez
(74) *Attorney, Agent, or Firm*—Andrea G. Reister; Covington & Burling LLP

(57) ABSTRACT

Inhalation device and associated method for facilitating inhalation by a patient of powder medicaments contained in a receptacle. The inhalation device has a chamber for receiving the receptacle. A ring is circumferentially coupled to an inner surface of the chamber to achieve a higher reproducible emitted dose of medicament from the receptacle. The inhalation device also includes an improved implement for puncturing the receptacle, requiring less force and experiencing fewer failures.

17 Claims, 13 Drawing Sheets

U.S. PATENT DOCUMENTS

| | | |
|---|---|---|
| 4,860,740 A | 8/1989 | Kirk et al. |
| 4,889,114 A | 12/1989 | Kladders |
| 4,995,385 A | 2/1991 | Valentini et al. |
| 5,042,472 A | 8/1991 | Bunin |
| 5,152,284 A | 10/1992 | Valentini et al. |
| 5,239,991 A | 8/1993 | Chawla et al. |
| 5,239,992 A | 8/1993 | Bougamont et al. |
| 5,301,666 A | 4/1994 | Lerk et al. |
| 5,349,947 A | 9/1994 | Newhouse et al. |
| 5,437,271 A | 8/1995 | Hodson et al. |
| 5,507,281 A | 4/1996 | Kuhnel et al. |
| 5,524,613 A | 6/1996 | Haber et al. |
| 5,533,505 A | 7/1996 | Kallstrand et al. |
| 5,575,280 A | 11/1996 | Gupte et al. |
| 5,595,175 A | 1/1997 | Malcher et al. |
| 5,617,845 A | 4/1997 | Poss et al. |
| 5,647,349 A | 7/1997 | Ohki et al. |
| 5,651,359 A | 7/1997 | Bougamont et al. |
| 5,660,169 A | 8/1997 | Kallstrand et al. |
| 5,673,686 A | 10/1997 | Villax et al. |
| 5,685,294 A | 11/1997 | Gupte et al. |
| 5,699,789 A | 12/1997 | Hendricks |
| 5,727,546 A | 3/1998 | Clarke et al. |
| 5,740,794 A | 4/1998 | Smith et al. |
| 5,785,049 A | 7/1998 | Smith et al. |
| 5,787,881 A | 8/1998 | Chawla |
| 5,797,391 A | 8/1998 | Cook et al. |
| 5,810,004 A | 9/1998 | Ohki et al. |
| 5,829,434 A | 11/1998 | Ambrosio et al. |
| 5,860,419 A | 1/1999 | Davies et al. |
| 5,896,855 A | 4/1999 | Hobbs et al. |
| 5,918,594 A | 7/1999 | Asking et al. |
| 5,921,237 A | 7/1999 | Eisele et al. |
| 6,065,472 A | 5/2000 | Anderson et al. |
| 6,092,522 A | 7/2000 | Calvert et al. |
| 6,098,619 A | 8/2000 | Britto et al. |
| 6,102,035 A | 8/2000 | Asking et al. |
| 6,105,574 A | 8/2000 | Jahnsson |
| 6,116,237 A | 9/2000 | Schultz et al. |
| 6,116,238 A | 9/2000 | Jackson et al. |
| 6,119,853 A | 9/2000 | Garrill et al. |
| 6,142,145 A | 11/2000 | Dagsland et al. |
| 6,187,269 B1 | 2/2001 | Lancesseur et al. |
| 6,237,590 B1 | 5/2001 | Leedom et al. |
| 6,273,085 B1 | 8/2001 | Eisele et al. |
| 6,286,507 B1 | 9/2001 | Jahnsson |
| 6,332,461 B1 | 12/2001 | Hyppola |
| 6,390,291 B1 | 5/2002 | Garrill et al. |
| 6,575,160 B1 * | 6/2003 | Volgyesi ................ 128/203.15 |
| 6,705,313 B1 * | 3/2004 | Niccolai ................ 128/203.21 |
| 6,732,732 B1 * | 5/2004 | Edwards et al. ....... 128/203.21 |
| 6,766,799 B1 * | 7/2004 | Edwards et al. ....... 128/203.15 |
| 2003/0094173 A1 | 5/2003 | Burr et al. |
| 2004/0154619 A1 * | 8/2004 | Edwards et al. |
| 2005/0022812 A1 * | 2/2005 | Hrkach |
| 2005/0051166 A1 * | 3/2005 | Glusker et al. ........ 128/203.21 |

FOREIGN PATENT DOCUMENTS

| | | |
|---|---|---|
| WO | WO 00/64519 A1 | 11/2000 |
| WO | WO 01/07107 | 2/2001 |

OTHER PUBLICATIONS de Boer, A.H. et al., "Inhalation characteristics and their effects on in vitro drug delivery from dry powder inhalers, Part 1. Inhalation characteristics, work of breathing and volunteers' preference in dependence of the inhaler resistance," International Journal of Pharamaceutics 130: 231-244 (1996).

Dunbar, Craig A. et al., A Comparison of Dry Powder Inhaler Dose Delivery Characterisitics Using a Power Criterion, PDA Journal of Pharmaceutical Science & Technology, 54(6): 4780484, Nov./Dec. 2000.

Feddah, Majid R. et al., In-Vitro Characterisation of Metered Dose Inhaler Versus Dry Powder Inhaler Glucocorticoid Products: Influence of Inspiratory Flow Rates, J. Pham. Pharmaceut. Sci. (www.ualberta.ca/-csps) 3(3): 317-324 (2000).

Koskela, T. et al., Efficacy of salbutamol via Easyhaler@ unaffected by low inspiratory flow, Respiratory Medicine 94: 1229-1233 (Dec. 2000).

Nielsen, K.G. et al., Flow-dependent effect of formoterol drypowder inhaled from the Aerolizer@, European Respiratory Journal, 10: 2105-2109 (Sep. 1997).

Richards, Robert and Saunders, Michael, Need for a comparative performance standard for dry powder inhalers, Thorax 48: 1186-1187 (Nov. 1993).

Ross, Danna L. and Schultz, Robert K., Effect of Inhalation Flow Rate on the Dosing Characteristics of Dry Powder Inhaler (DPI) and Metered Dose Inhaler (MDI) Products, Journal of Aerosol Medicine, 9: 215-226 (Nov. 2, 1996).

Smith, Karen J. et al., Influence of Flow Rate on Aerosole Particle Size Distributions from Pressurized and Breath-Actuated Inhalers, Journal of Aerosol Medicine, 11: 231-245 (Nov. 4, 1998).

* cited by examiner

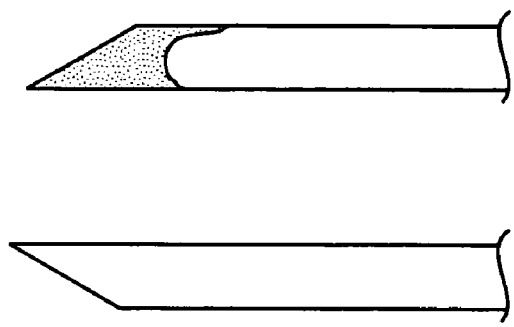
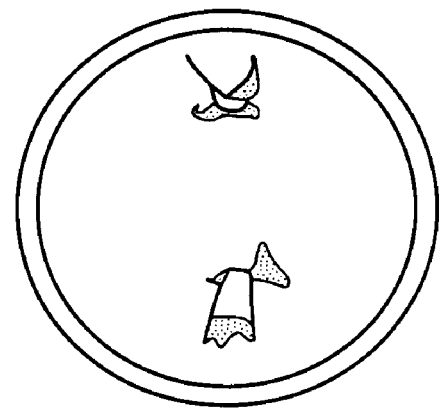
FIG. 9A  FIG. 9B
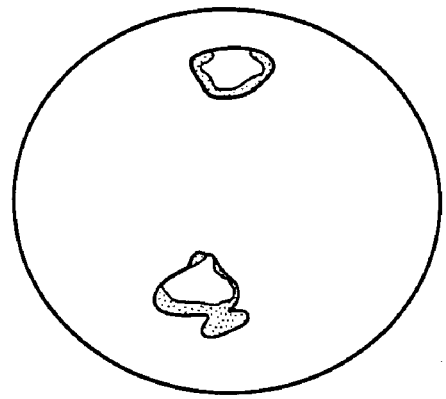
FIG. 8

☒ 6 MG FILL WEIGHT (C2): ED=5.6MG; FPM=4.5MG
☒ 50 MG FILL WEIGHT (C30): ED=49.1MG; FPM=37.2MG

INHALATION DEVICE AND METHOD

CROSS-REFERENCE TO RELATED APPLICATIONS

The present application is a divisional of application Ser. No. 09/835,302, filed Apr. 16, 2001, now U.S. Pat. No. 6,766,799, the entirety of which is incorporated herein by reference.

BACKGROUND OF THE INVENTION

1. Field of the Invention

The present invention relates generally to facilitating release of powder contained in a receptacle. More specifically, the present invention relates to the administration of medication by a method and apparatus for facilitating inhalation of powder medicaments.

2. Related Art

In the medical field, it is often desirable to administer various forms of medication to patients. Well known methods of introducing medication into the human body include the oral ingestion of capsules and tablets, intravenous injection through hypodermic needles, and numerous others. In one method, certain medications may be inhaled into a patient's respiratory tract and lungs through the nose or mouth. Certain of these medications, such as bronchodilators, corticosteroids, etc., for the treatment of asthma and other respiratory anomalies, may be aimed at the respiratory tract directly. Others are inhaled for purposes of systemic treatment, i.e. for treatment of any area of the body through absorption from the respiratory tract through the lung tissue, into the deep lungs, and into the bloodstream. Each of these medications comes in a variety of forms, including fluids, which are commonly administered as an aerosol vapor or mist, as well as solids. Inhalable solids typically take the form of fine, dry powders. Specialized devices, such as inhalers, are provided to assist the patient in directing these fine powder medications into the respiratory tract.

Various types of inhalers are known for the administration of dry powder medicaments. However, each of these inhalers suffers certain drawbacks. For example, U.S. Pat. No. 5,787,881 discloses an inhaler that is used with encapsulated dry powder medicaments. However, use of this device requires numerous steps and imposes a number of inconveniences on a user. For example, the medication capsules used with the device have an aperture formed therein prior to insertion into an opening in the inhaler. Therefore, there exists a danger that an amount of medication may be lost prior to or during insertion into the device. After insertion of the capsule, use of the device requires the additional step that a cover must be closed before the medication may be inhaled.

Inhalation devices configured for use with a capsule containing some type of medicament are shown in U.S. Pat. No. 4,069,819 to Valentini et al. ("the '819 patent") and U.S. Pat. No. 4,995,385 to Valentini et al. ("the '385 patent"). The inhalation device described in the '385 patent was developed to overcome the drawbacks of the device described in the '819 patent. Particularly, in a large number of cases, the device described in the '819 patent experienced irregular and incomplete emptying of the capsule, thereby resulting in difficulties in properly administering the medicament in the capsule. The inhalation device described in the '385 patent attempts to overcome this deficiency by tapering the nebulization chamber toward the end surface that comprises the discharge holes. Thus, the nebulization chamber of the '385 patent is not cylindrical, but rather frusto-conical in form in an attempt to achieve regular complete emptying of the nebulization chamber. However, further improvements in the design of inhalation devices are needed to achieve a higher emitted dose. As used herein, "emitted dose" refers to the percentage of the dose of powder medicament, contained in a receptacle in the inhalation device, that is emitted from the inhalation device. Moreover, improvements are needed to achieve higher emitted doses that are consistently reproducible, i.e., with low standard deviation. There is a particular need in the art for high, reproducible emitted doses at low flow rates, as well as for high dosage ranges.

Another drawback of the inhalation devices described in the '819 and the '385 patents is the piercing device that is used to puncture the capsule. Such conventional piercing devices are formed from circular stock, with the points created by pinching the stock at an angle, thereby creating a single sharp cutting edge. Drawbacks of such a design are that the point (which must puncture the capsule material) is often rounded, lessening its effectiveness as a piercing device. Moreover, burrs often form on the lower edge, which can stop the piercing device from retracting from the capsule, thereby causing a device failure. The holes formed by such a conventional piercing device are generally round, and do not have the appearance of being cut by a sharp edge. With such a conventional design, the capsule is often crushed, rather than punctured or pierced. If such a conventional piercing device is used with brittle capsule materials such as gelatin, pieces of capsule material of a size that can be inhaled are usually broken off from the capsule. Thus, conventional piercing devices are less than optimal, particularly for brittle capsule material.

Thus, there is a need in the art for an improved method and apparatus for inhalation of dry powder medicaments. What is needed is an inhaler that provides for a higher emitted dose that is consistently reproducible with low standard deviation. Such a need is particularly acute for low flow rates, and for high dosage ranges. There is a further need in the art for an improved means for puncturing the capsule containing the medicament. The present invention, the description of which is fully set forth below, solves the need in the art for such improved methods and apparatus.

SUMMARY OF THE INVENTION

The present invention relates to a method and apparatus for facilitating release of powder from a device. In one aspect of the invention, a device for emitting powder is provided. The device includes a first casing portion, and a second casing portion removably coupled to the first casing portion. A cylindrical chamber, defined by a straight wall of circular cross section, is coupled to the first casing portion. The chamber has a proximal end and a distal end. A ring is circumferentially coupled to an inner surface of the chamber. The ring is preferably disposed at approximately a midpoint of the chamber, or, alternatively, disposed adjacent the proximal end of the chamber. The second casing portion includes an emitter portion disposed at the proximal end of the chamber when the first and second casing portions are coupled together. The emitter portion defines at least one aperture configured to emit powder therethrough.

In another aspect of the present invention, the device is configured as an inhalation device for administering powder. In this aspect of the present invention, the emitter portion is configured as an inhalation portion so that powder is dispersed in the chamber and administered to a user through the inhalation portion. The inhalation portion may be configured as a mouth piece for inhalation through the mouth, or as a nose piece for inhalation through the nose.

In one aspect of the invention, the powder is contained in a receptacle that is disposed in the chamber. Upon puncturing the receptacle, powder is dispersed in the chamber and emitted or inhaled from the device.

In yet another aspect of the present invention, the device of the present invention includes means for puncturing the receptacle. The means for puncturing can be configured as a staple. Such a staple is preferably configured in a substantially U-shape, having two prongs. In one aspect of the present invention, each of the prongs has a square cross-section. In another aspect of the present invention, the substantially U-shaped staple includes a rounded portion and two prongs that define a non-planar inner edge and a non-planar outer edge of the staple, the staple being formed from a rectangular length having two end surfaces and four planar side surfaces that intersect to form four non-planar edges. The inner edge of the staple is configured to be one of the non-planar edges, and the outer edge of the staple is the non-planar edge that is opposite that non-planar edge. Each end surface is an angled diamond-shaped surface. In a preferred aspect, each end surface has a top point at an apex of the inner edge, and a bottom point at an apex of the outer edge, each top point forming a cutting point for one of the prongs.

In still a further aspect of the present invention, a method for dispensing powder by inhalation is provided. Such a method comprises providing a powder inhalation device, the device comprising
a first casing portion,
a cylindrical chamber, defined by a straight wall of circular cross-section, coupled to said first casing portion, said chamber having a proximal end and a distal end and configured to receive a receptacle therein, said chamber comprising a ring circumferentially coupled to an inner surface of said chamber, and
a second casing portion removably coupled to said first casing portion, said second casing portion comprising an inhalation portion disposed at the proximal end of said chamber when said first and said second casing portions are coupled, said inhalation portion comprising a hemispheric region defining a plurality of apertures configured to emit powder therethrough;
puncturing the receptacle to disperse powder in said chamber; and
inhaling the powder through said inhalation portion.

In one aspect of the present invention, the inhaling step is carried out by inhaling the powder through a mouthpiece into a user's mouth. Alternatively, the inhaling step may be carried out by inhaling the powder through a nose piece into a user's nose.

Features and Advantages

One feature of the present invention is that it provides high emitted doses that are consistently reproducible over a range of flow rates and dosage quantity. Advantageously, the present invention improves the emitted dose at both low flow rates and high dose ranges. A particularly advantageous feature of the present invention is its ability to operate at low flow rates, such as would be associated with a child or a person with a respiratory disease.

One advantage of the present invention is that the preferred means for puncturing used in the device is less expensive to manufacture than conventional piercing devices. Moreover, the means for puncturing of the present invention advantageously provides improved puncturing performance since less force is needed to puncture the receptacles, and fewer failures result than with conventional piercing devices.

Another advantage of the preferred means for puncturing is an improvement to the flow rate independence of the inhaler. Consequently, the powdered medicament delivered to a patient will be independent of how fast the patient breathes, thereby ensuring that a consistent dose of medicament is delivered each time.

Another advantageous feature of the present invention is the accuracy of medicament dosage delivered thereby. Since only one dosage of medication is present in the inhaler during each use, the possibility of overdose is eliminated, and the medicament need not be metered prior to delivery. A patient may simply inhale all medicament present in the device.

Because the present invention operates only under the inhalative power of the patient, the inhaler carries the additional advantage that no accessory device, such as a compressed air cylinder or other propellant, needs to be used in conjunction with the present invention.

Another advantage of the present invention is that during inhalation, the medicament is subjected to mixing in the dispersion chamber. This helps to ensure that the medicament exiting the inhaler and entering the patient's respiratory system is in the form of a fine dry powder, facilitating medicament deposition in the lungs. In addition, inhalation of finer powders is typically more comfortable for the patient.

Still another advantage of the present invention is that it can be used with individuals who cannot breathe hard, such as a child or an- asthmatic, or individuals who are sleeping or in a coma.

Yet another advantage of the apparatus of the present invention is that it is reusable. To reuse, a patient removes the emptied receptacle, and replaces it with a fresh receptacle filled with the proper dose of medicament.

BRIEF DESCRIPTION OF THE FIGURES

The present invention is described with reference to the accompanying drawings. In the drawings, like reference numbers indicate identical or functionally similar elements.

FIG. 8 shows the puncture obtained with the staple shown in FIGS. 7A through 7D;

FIG. 9A shows a partial view of another embodiment of a staple suitable for use with the device of the present invention;

FIG. 9B illustrates the puncture obtained with the staple shown in FIG. 9A;

FIG. 12 is a bar graph showing a comparison of mass fraction distributions obtained for 6 mg (left bar) and 50 mg (right bar) fill weights;

FIG. 13 is a graph showing glucose levels (mg/dL) in beagle dogs after administration of insulin using an aerosol generator and a device of the present invention with the low ring configuration substantially as shown in FIG. 4;

DETAILED DESCRIPTION OF THE PREFERRED EMBODIMENTS

Overview

Figure 1:
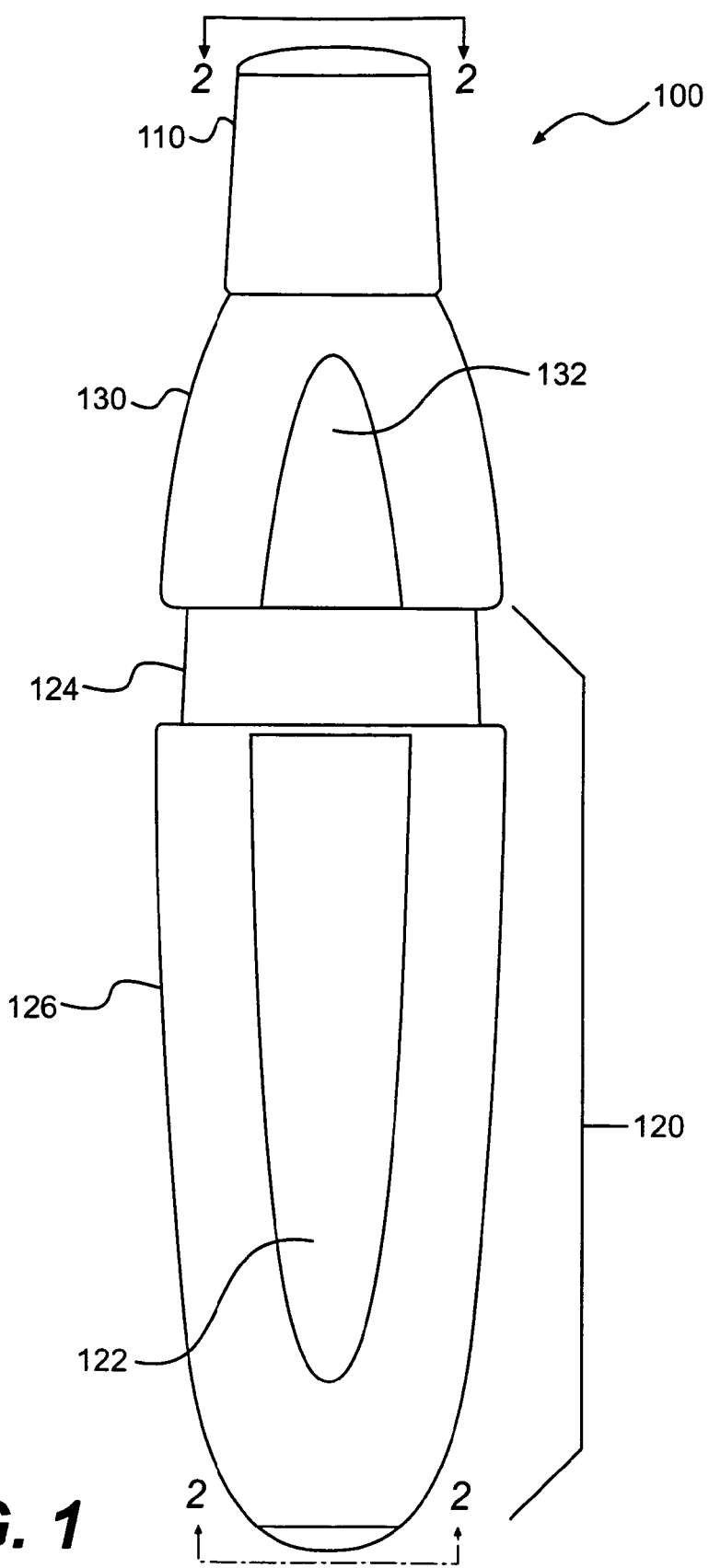
FIG. 1 is a front view of one embodiment of a device of the present invention.

The present invention provides an improved method and apparatus for facilitating release of powder. In a preferred embodiment, the powder is contained in a receptacle. As used herein, the term "receptacle" includes but is not limited to, for example, a capsule, blister, film covered container well, chamber, and other suitable means of storing a powder known to those skilled in the art. The present invention will be described below in the context of a method and apparatus for dispensing dry powder medicaments for inhalation by a patient. However, it should be apparent to one skilled in the art that the invention is not limited to such an exemplary embodiment, and could be used for other purposes.

As will be described in more detail below, an apparatus of the present invention is an inhaler that includes a chamber. In one embodiment, the chamber is configured to receive the receptacle containing the medicament. To improve the emptying of the receptacle and provide a higher reproducible emitted dose, the chamber includes a ring circumferentially coupled to an inner surface of the chamber. The ring is preferably disposed at approximately a midpoint of the chamber, or alternatively, adjacent the proximal end of the chamber. In proper use, air will exit the inhaler carrying a full dose of medicament in the form of a fine, dry powder.

The inhaler of the present invention is preferably configured with a means for puncturing the receptacle that improves puncturing performance, particularly with brittle receptacle material. The means for puncturing the receptacle of the present invention is preferably configured as a substantially U-shaped staple with two prongs, each prong having a sharp point and two cutting edges. In one embodiment of the present invention, each prong has a square cross-section, with the staple material being bent around a face so that the innermost part of the U-shaped staple is flat. In another embodiment of the present invention, the staple material is rotated 45 degrees so that it is bent around an edge so that the innermost part of the U-shaped staple is an edge. In such an embodiment, the end surface of each prong is an angled diamond-shaped surface.

The methods of the present invention use an inhaler to dispense powder by inhalation. As will be discussed in greater detail below, a user operates the device to puncture the receptacle to disperse powder in the chamber, and inhales the powder through the inhalation portion.

Inhaler and Associated Method of the Present Invention

A front view of one embodiment of an inhalation device 100 of the present invention is shown in FIG. 1. The rear view of device 100 is substantially identical to the front view. Device 100 includes a first or lower casing portion 120 and a second or upper casing portion 130 removably coupled to first casing portion 120. Upper casing portion 130 and lower casing portion 120 include a flattened region 132 and 122, respectively, for ease of gripping the casing for use by a patient. Lower casing portion 120 preferably includes an outer casing 126 and an inner casing 124 movably received within outer casing 126. A removable cap 110 is provided at the user or inhalation end of the device.

Preferred materials for device 100 include Food and Drug Administration (FDA) approved, USP tested plastics. Preferably, device 100 is manufactured using an injection molding process, the details of which would be readily apparent to one skilled in the art.

FIG. 2 is a cross-section of device 100 shown in FIG. 1 along line 2—2. As shown in FIG. 2, device 100 includes an inhalation or emitter portion 220. Inhalation portion 220 comprises a hemispheric region 222 that defines a plurality of apertures 224. It should be understood that the present invention is not limited to a particular number of apertures 224, and can be configured such that at least one aperture 224 is provided. An inhalation piece 226 is provided to allow for inhalation of the medicament by a user. Inhalation piece 226 can be configured as a mouth piece for inhalation through a user's mouth. Alternatively, inhalation piece 226 can be configured as a nose piece for inhalation through a user's nose.

Device 100 includes a cylindrical chamber 210 that is defined by a straight wall 212 of circular cross-section. Chamber 210 has a proximal end 214 and a distal end 216. A plurality of slits 218 are defined by wall 212, and are configured for introducing air into chamber 210 to disperse powder released from a capsule 219. It should be understood that the present invention is not limited to a particular number of slits 218, and can be configured such that at least one slit 218 is provided. Powder released from capsule 219 is dispersed in chamber 210 and inhaled through apertures 224 and inhalation piece 226 by the user.

In other embodiments of the invention, receptacles other than capsules are used, such as blisters and film covered container wells as is known in the art. In one embodiment, the volume of the receptacle is at least about 0.37 $cm^3$. In another embodiment, the volume of the receptacle is at least about 0.48 $cm^3$. In yet another embodiment, the receptacles have a volume of at least about 0.67 $cm^3$ or 0.95 $cm^3$ . In one embodiment of the invention, the receptacle is a capsule designated with a capsule size 2, 1, 0, 00, or 000. Suitable capsules can be obtained, for example, from Shionogi (Rockville, Md.). Blisters can be obtained, for example, from Hueck Foils, (Wall, N.J.).

The receptacle encloses or stores particles, also referred to herein as powders. The receptacle is filled with particles in a manner known to one skilled in the art. For example, vacuum filling or tamping technologies may be used. Generally, filling the receptacle with powder can be carried out by methods known in the art. In one embodiment of the invention, the particle or powder enclosed or stored in the receptacle have a mass of about 5 milligrams (mg). Preferably the mass of the particles stored or enclosed in the receptacle is at least about 10 mg.

In one embodiment of the present invention, particles used with the device have a tap density of less than about 0.4 g/cm$^3$. Particles having a tap density of less than about 0.4 g/cm$^3$ are referred to herein as "aerodynamically light". In a preferred embodiment, the particles have a tap density of near to or less than about 0.1 g/cm$^3$. Tap density is a measure of the envelope mass density characterizing a particle. The envelope mass density of particles of a statistically isotropic shape is defined as the mass of the particle divided by the minimum sphere envelope volume within which it can be enclosed. Features that can contribute to low tap density include irregular surface texture and hollow or porous structure. Particularly preferred particles and powders are described in U.S. Pat. Nos. 6,136,295, 5,985,309, 5,874,064, and 5,855,913, and U.S. patent application Ser. No. 09/591,307, filed Jun. 9, 2000 entitled "High Efficient Delivery of a Large Therapeutic Mass Aerosol", the entirety of each of the foregoing patents and patent applications is hereby incorporated herein by reference.

Device 100 includes a means for puncturing 230 that is used to puncture capsule 219 to release powder contained therein into chamber 210. In the embodiment shown in FIG. 1, means for puncturing 230 is configured as a substantially U-shaped staple having two prongs 232. In this embodiment, each of prongs 232 is configured with a square cross-section 234, thereby providing a sharp point and two cutting edges. This will be discussed in more detail below with respect to FIGS. 9A and 9B. As discussed in more detail below, device 100 could alternatively be configured with the puncturing implement shown in FIGS. 7A through 7D. As can be readily appreciated by one skilled in the art, the present invention is not limited to use of a substantially U-shaped staple as the means for puncturing the capsule. Alternatively, one, or a plurality of, straight needle-like implements could be used. Preferably, the puncturing implement is configured to puncture at least two holes in the capsule.

Means for puncturing 230 is preferably configured to be movable between a non-puncturing position (as depicted in FIG. 1) and a puncturing position. In the puncturing position, prongs 232 pierce or puncture capsule 219 to make holes therein. In a preferred embodiment, a means for biasing is provided that biases the means for puncturing 230 in the non-puncturing position. In the embodiment shown in FIG. 2, the means for biasing is configured as a spring 242 that biases the substantially U-shaped staple in the non-puncturing position.

Figure 2:
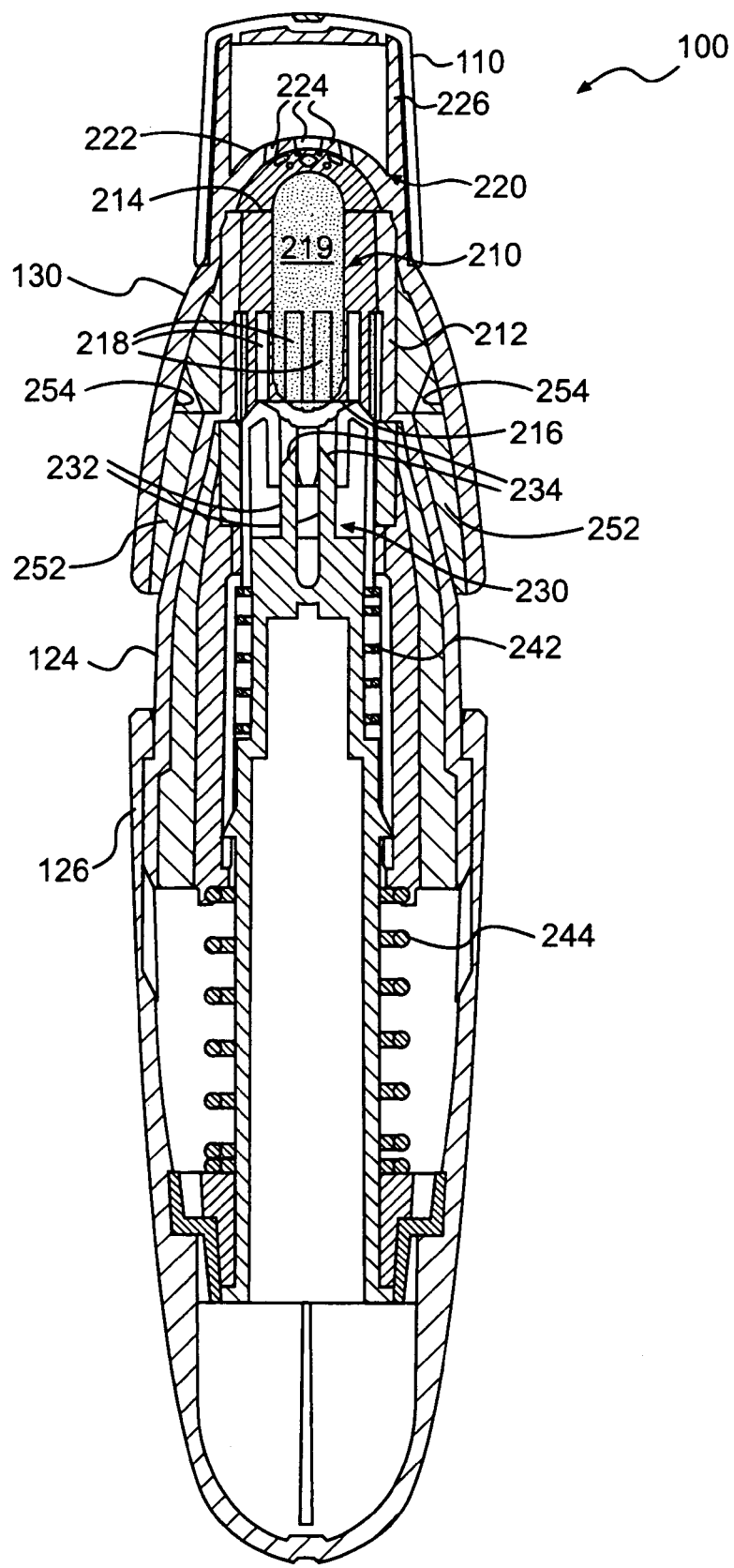
FIG. 2 is a cross-section of the device shown in FIG. 1 along line 2—2.

As noted with respect to FIG. 1, device 100 includes inner casing 124 and outer casing 126. As shown in FIG. 2, a spring 244 is disposed in lower casing portion 120 that biases inner casing 124 in an outward position. Upon compression of spring 244, inner casing 124 moves from the outward position to an inward position, thereby drawing lower casing portion 120 toward upper casing portion 130. Compression of spring 244 also causes compression of spring 242, thereby causing means for puncturing 230 to move to the puncturing position. Upon release of compression, springs 242 and 244 return to their biased state, thereby returning means for puncturing 230 to its non-puncturing position, and inner casing 124 to its outward position.

A pair of flanges 252 is disposed on first casing portion 120. A pair of grooves 254 is disposed on second casing portion 130 so that flanges 252 can be received within grooves 254 to thereby couple the first and second casing portions. Preferably, the first and second casing portions are coupled with a friction-fit engagement. A friction-fit engagement can be achieved using the groove and flange arrangement depicted in FIG. 2. Other alternative configurations for a friction-fit engagement would be readily apparent to one skilled in the art.

Figure 3:
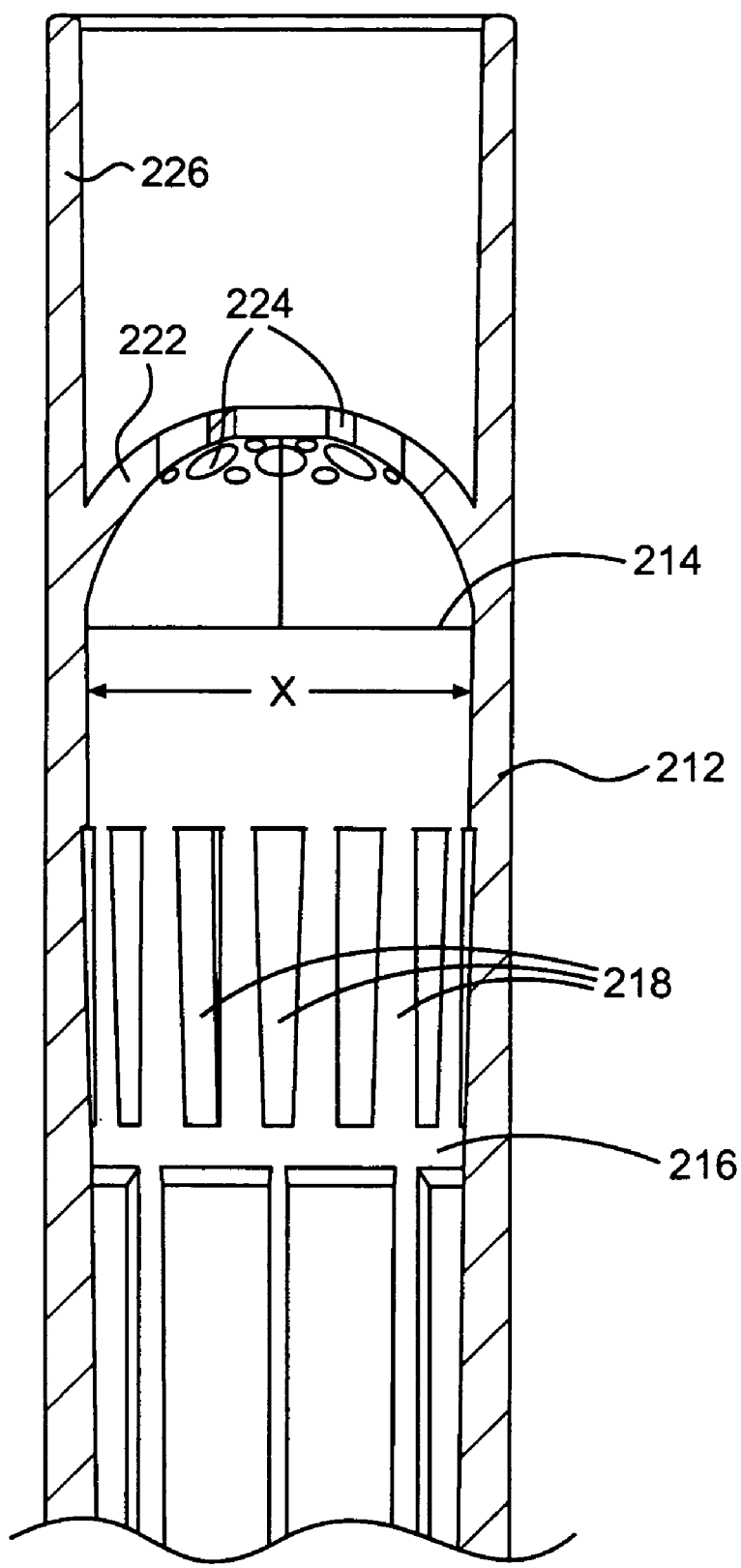
FIG. 3 is an enlarged partial cross-section of one embodiment of a dispersion chamber of the present invention.

FIG. 3 is an enlarged partial cross-section of one embodiment of chamber 210. In the embodiment shown in FIG. 3, chamber 210 does not contain a ring disposed on an inner surface, and an inner diameter of chamber 210 is depicted as "X". Such a configuration may be referred to herein as a "straight" chamber configuration.

Figure 4:
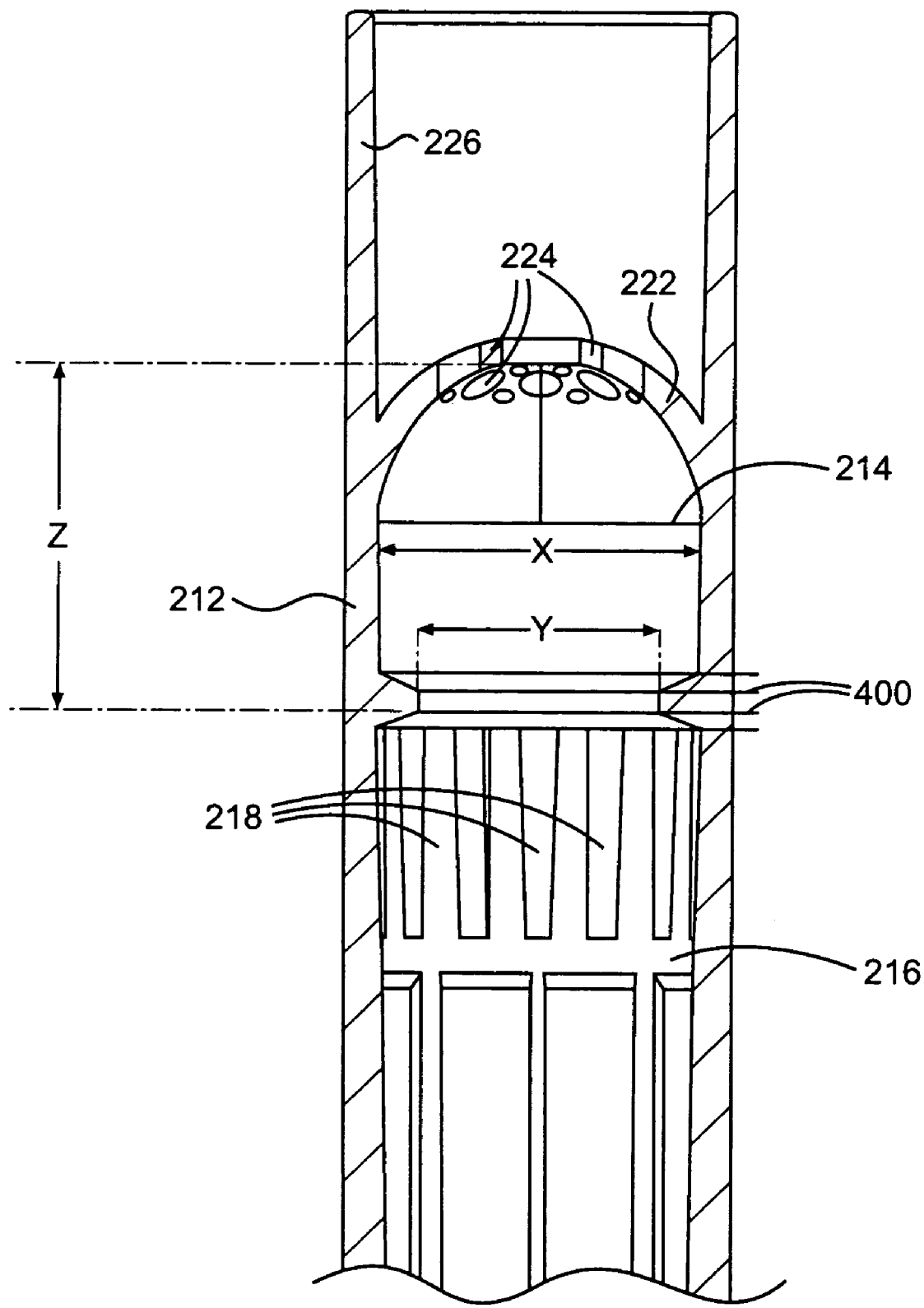
FIG. 4 is an enlarged partial cross-section of another embodiment of a dispersion chamber of the present invention showing one location for a ring in the dispersion chamber.

FIG. 4 is an enlarged partial cross-section of another embodiment of chamber 210. In the embodiment shown in FIG. 4, a ring 400 is circumferentially coupled to an inner surface of chamber 210. An inner diameter of ring 400 is depicted as "Y", and is less than inner diameter X of chamber 210. In the embodiment shown in FIG. 4, ring 400 is disposed at approximately a midpoint of chamber 210. Such a configuration may be referred to herein as a "low" ring position or "low" chamber configuration. As shown in FIG. 4, in the low ring position, ring 400 is disposed adjacent slits 218. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 4, diameter X is 0.47 in., diameter Y is 0.38 in., and distance Z is 0.49 in.

Figure 6:
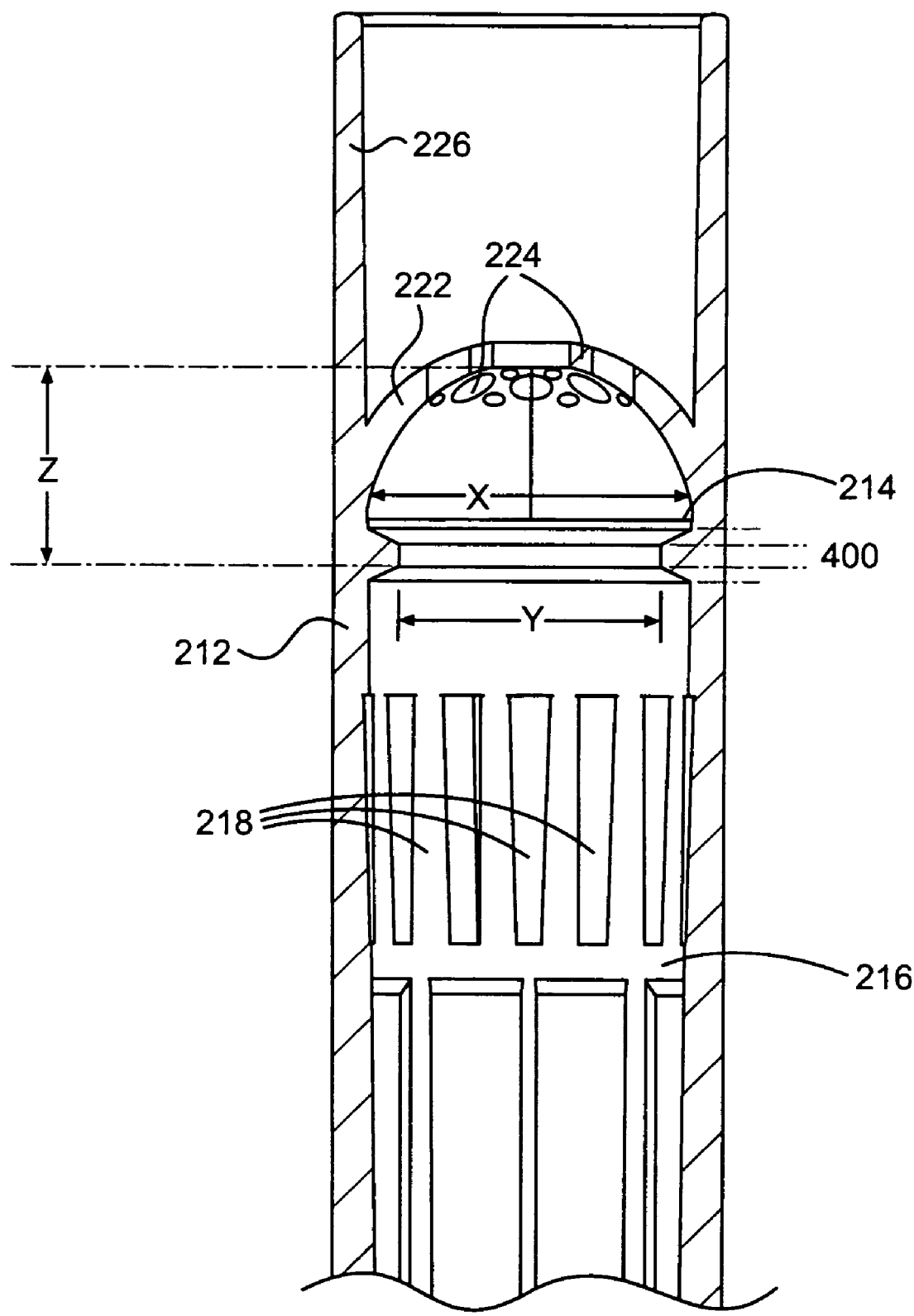
FIG. 6 is an enlarged partial cross-section of another embodiment of a dispersion chamber of the present invention showing another location for a ring in the dispersion chamber.

FIG. 6 is an enlarged partial cross-section of another embodiment of chamber 210. In the embodiment shown in FIG. 6, ring 400 is circumferentially coupled to an inner surface of chamber 210. An inner diameter of ring 400 is depicted as "Y", and is less than inner diameter X of chamber 210. In the embodiment shown in FIG. 6, ring 400 is disposed adjacent the proximal end of chamber 210. Such a configuration may be referred to herein as a "high" ring position or a "high" chamber configuration. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 6, diameter X is 0.47 in., diameter Y is 0.38 in., and distance Z is 0.29 in.

Figure 5:
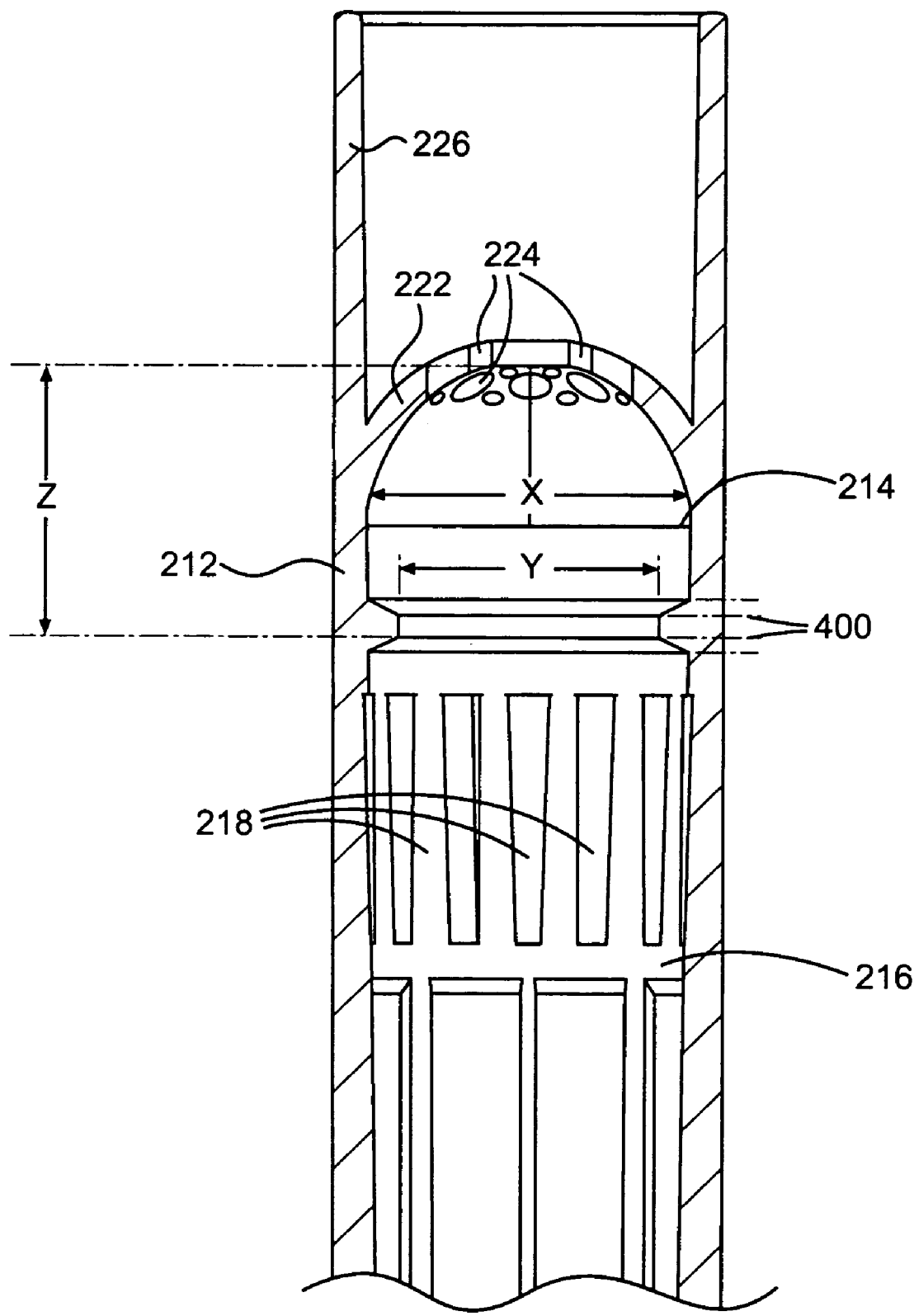
FIG. 5 is an enlarged partial cross-section of another embodiment of a dispersion chamber of the present invention showing another location for a ring in the dispersion chamber.

FIG. 5 is an enlarged partial cross-section of another embodiment of chamber 210. In the embodiment shown in FIG. 5, ring 400 is circumferentially coupled to an inner surface of chamber 210. An inner diameter of ring 400 is depicted as "Y", and is less than inner diameter X of chamber 210. In the embodiment shown in FIG. 5, ring 400 is disposed between the low ring position of FIG. 4 and the high ring position of FIG. 6. Such a configuration may be referred to herein as a "mid" ring position or "mid" chamber configuration. The ring position is measured by the distance from the top of hemispheric region 222 to the bottom edge of ring 400. This distance is depicted as "Z". The following dimensions are provided as exemplary dimensions of a device of the present invention. It should be understood by one skilled in the art that the present invention is not limited to the dimensions provided herein, or to any particular dimensions. In one embodiment of the chamber 210 shown in FIG. 5, diameter X is 0.47 in., diameter Y is 0.38 in., and distance Z is 0.39 in.

In one embodiment of the present invention, ring 400 is integral with chamber 210. In such an embodiment, ring 400 and chamber 210 are formed as a unit, such as through an injection molding, extrusion or a casting process. In another embodiment of the present invention, ring 400 is attached to the inner surface of chamber 210 in a manner known to those skilled in the art, such as through the use of glue or other type of adhesive, or by using an attaching device such as a pin or screw, etc. Preferably, the casing of device 100 is made from a material that can be injection molded, such as a plastic material (preferably FDA approved, USP tested). As would be readily apparent to one skilled in the art, the material is preferably durable, easy to clean, and non-reactive with powder medicaments.

Figure 15:
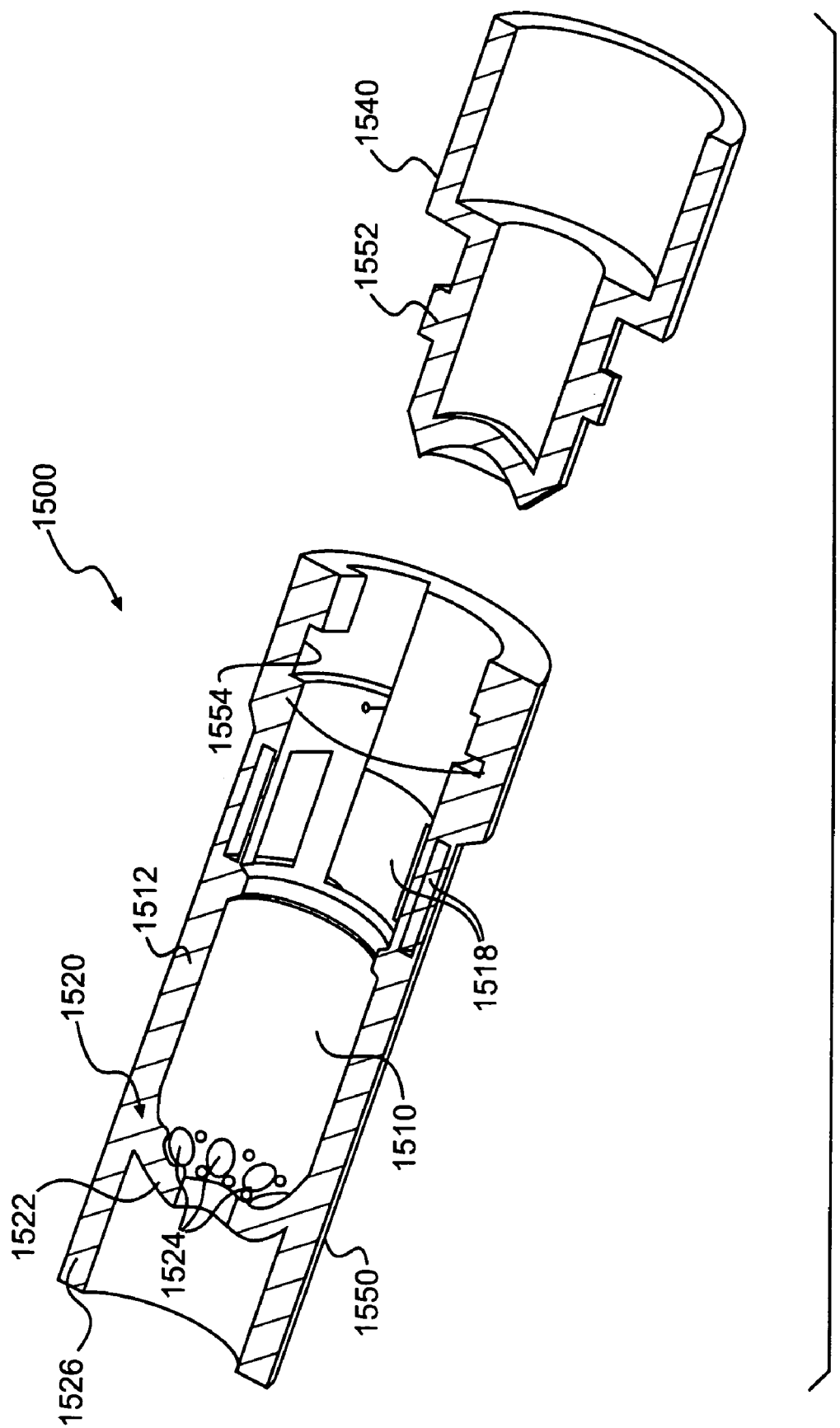
FIG. 15 is an exploded cross-sectional view of an alternate embodiment of a device of the present invention.

An exploded cross-sectional view of an alternate embodiment of a device 1500 of the present invention is shown in FIG. 15. Device 1500 includes a first or lower casing portion 1540 and a second or upper casing portion 1550 removably coupled to first casing portion 1540. First and second casing portions 1540 and 1550 are coupled through the use of a flange 1552 and a groove 1554. Preferred materials for device 1500 include Food and Drug Administration (FDA) approved, USP tested plastics. Preferably, device 1500 is manufactured using an injection molding process, the details of which would be readily apparent to one skilled in the art.

Device 1500 includes an inhalation or emitter portion 1520. Inhalation portion 1520 comprises a hemispheric region 1522 that defines a plurality of apertures 1524. It should be understood that the present invention is not limited to a particular number of apertures 1524, and can be configured such that at least one aperture 1524 is provided. An inhalation piece 1526 is provided to allow for inhalation of the medicament by a user. Inhalation piece 1526 can be configured as a mouth piece for inhalation through a user's mouth. Alternatively, inhalation piece 1526 can be configured as a nose piece for inhalation through a user's nose.

Device 1500 includes a cylindrical chamber 1510 that is defined by a straight wall 1512 of circular cross-section. A plurality of slits 1518 are defined by wall 1512, and are configured for introducing air into chamber 1510 to disperse powder released from, for example, capsule 219 as illustrated in FIG. 2. It should be understood that the present invention is not limited to a particular number of slits 1518, and can be configured such that at least one slit 1518 is provided. Powder released from capsule 219 is dispersed in chamber 1510 and inhaled through apertures 1524 and inhalation piece 1526 by the user.

As would be readily apparent to one skilled in the art, device 1500 can be configured with means for puncturing and means for biasing in a manner similar to that described above with respect to the embodiment shown in FIGS. 1 and 2. Means for puncturing are described in more detail below with respect to FIGS. 7A through 7D, 8, 9A, and 9B. Moreover, device 1500 can be configured with the chamber designs described above with respect to FIGS. 3–6.

Figure 10:
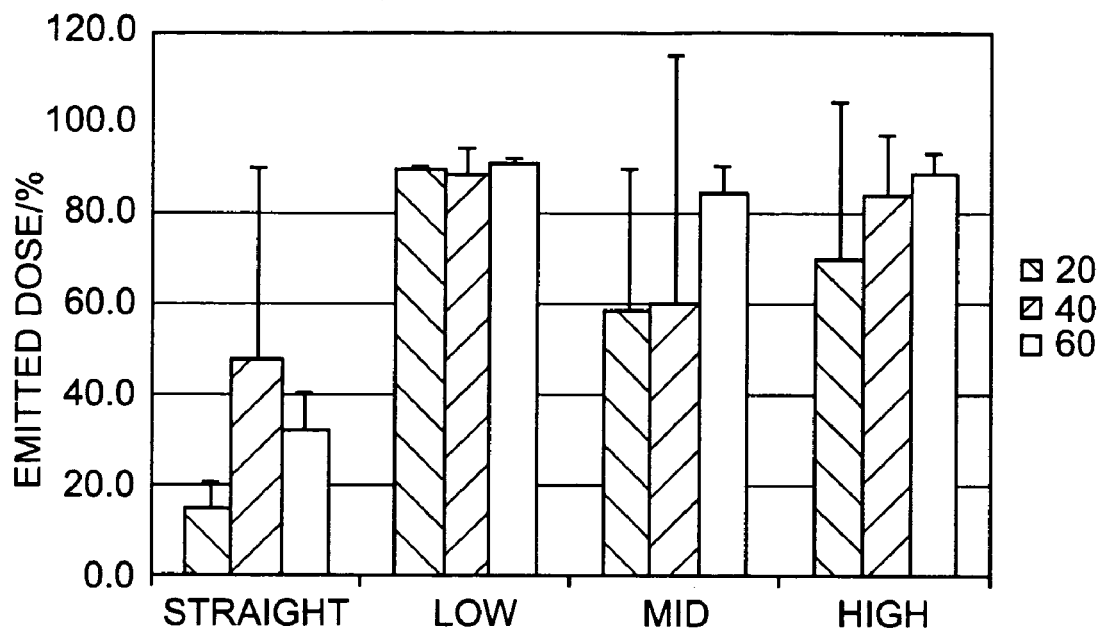
FIG. 10 is a bar graph illustrating emitted dose at flow rates of 20 L/min (left bar), 40 L/min (center bar), and 60 L/min (right bar) for four dispersion chamber configurations.

FIG. 10 is a bar graph illustrating emitted dose at flow rates of 20 L/min (left bar), 40 L/min (center bar), and 60 L/min (right bar) for a total volume of 2 L for four dispersion chamber configurations (standard deviations shown; sample size n=3). The flow rates were measured with a flow meter. The emitted dose measurement involved placing a capsule into four embodiments of the inhaler of the present invention for actuation into an emitted dose (ED) measurement apparatus. The ED apparatus included a powder filter and a filter holder. The powder collected by the ED apparatus was quantified by fluorescence spectrophotometry. The straight configuration is shown in FIG. 3; the low configuration is shown in FIG. 4; the mid configuration is shown in FIG. 5; and the high configuration is shown in FIG. 6. As can be seen from FIG. 10, each of the low, mid, and high configurations demonstrated a higher emitted dose at each of the three flow rates than the straight (no ring) configuration. Thus, the ring configuration of the present invention provides an improvement over conventional chamber designs without a ring, such as those shown in the '819 and '385 patents. At each of the flow rates shown in FIG. 10, the low configuration produced a higher emitted dose and a lower standard deviation than the mid and high configurations.

Figure 11:
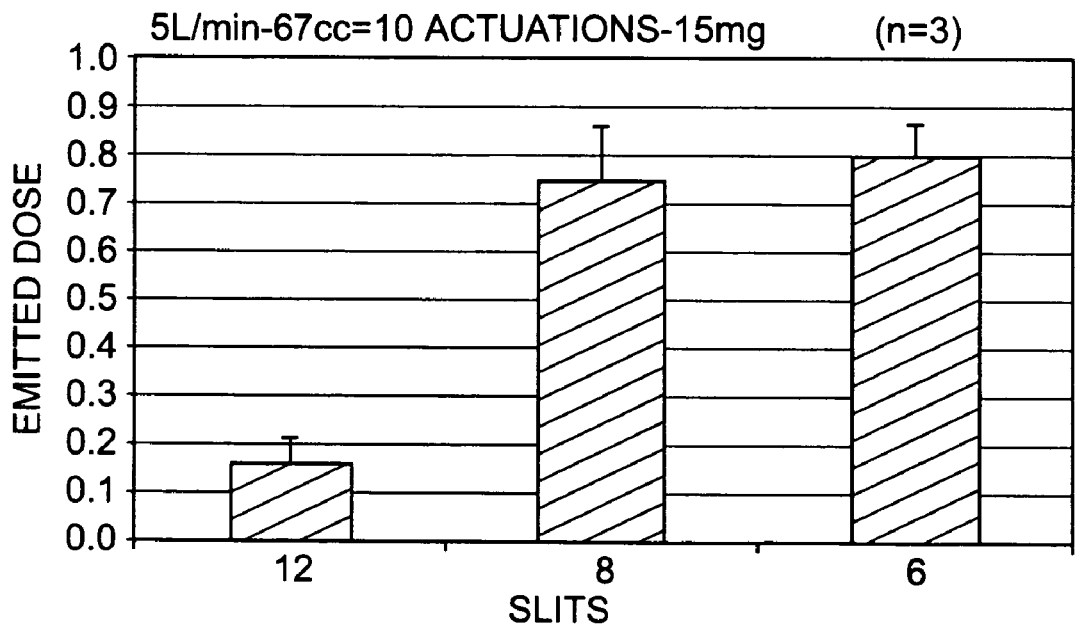
FIG. 11 is a bar graph illustrating emitted dose at low flow rates for devices with varying numbers of slits.

FIG. 11 is a bar graph illustrating emitted dose at low flow rates for devices with varying numbers of slits 218. A flow rate of less than about 15 L/min will be referred to herein as a "low flow rate." The measurements were taken at a flow rate of 5 L/min, with a volume of 67 cc and a 15 mg dosage. As show in FIG. 11, by decreasing the number of slits 218, the emitted dose increases so that the device of the present invention successfully delivers a high emitted dose at low flow rate over multiple (ten) actuations. Thus, the device of the present invention achieves a high emitted dose at low flow rates that is consistently reproducible with low standard deviation.

Figure 14:
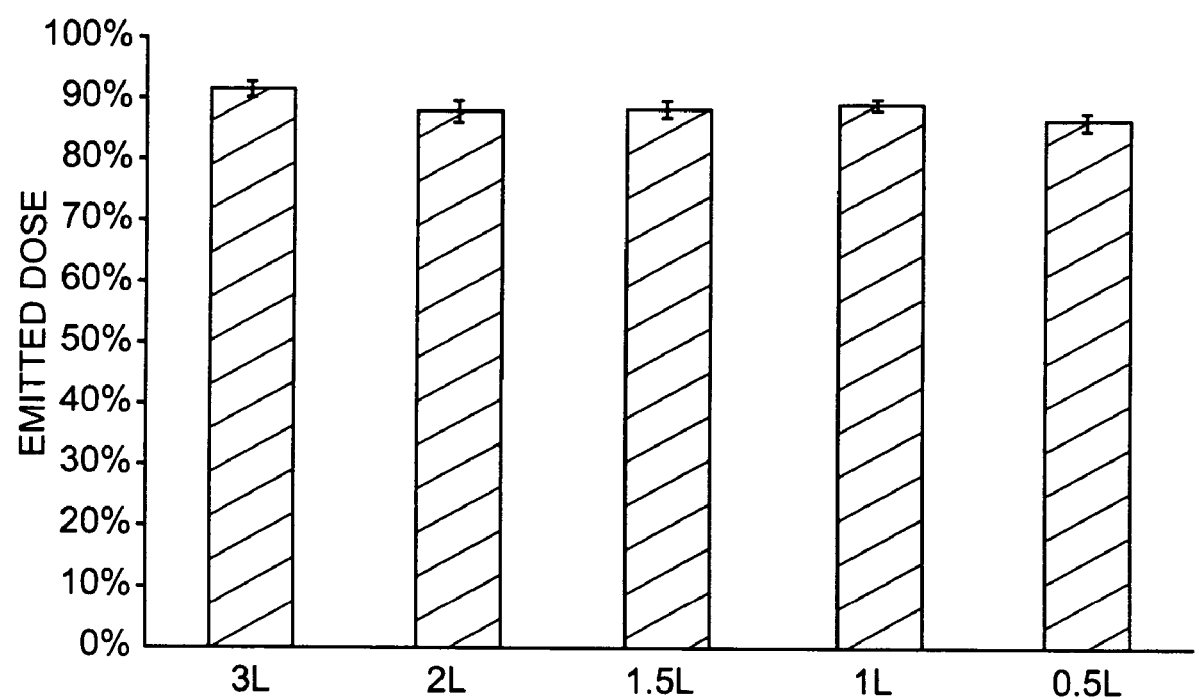
FIG. 14 is a bar graph illustrating the percentage emitted dose as a function of air volume.

Experiments were conducted to evaluate the emitted dose as a function of air volume drawn through the inhaler. The inhaler was operated at a constant flow rate of 30 L/min for a 5 mg dose. The volume of air through the inhaler was varied by varying the actuation time. Volumes of 0.5, 1.0, 1.5, 2.0 and 3.0 L were investigated. FIG. 14 shows the percentage emitted dose as a function of air volume (n=3, standard deviations shown). The emitted dose remained constant across the range of volumes and was consistently reproducible with low standard deviation.

In the embodiments having the inner diameter X of chamber 210 of 0.47 in. and the inner diameter Y of ring 400 of 0.38 in., the ratio of the inner diameter of the ring to the inner diameter of the chamber is about 0.8. By modifying the inner diameters of the ring and the chamber, it is possible to optimize the emitted dose at varying flow rates. As reported in Annals of the ICRP, Human respiratory tract model for radiological protection, 24 (1–3), Elsevier Science, Inc., New York, 1994, the flow rate for a tidal breathing seated adult male is 300 mL/s (18 L/min) for a volume of 750 mL. In one embodiment of a device of the present invention optimized for low flow rates (less than about 15 L/min), inner diameter X of chamber 210 is 0.33 in. and inner diameter Y of ring 400 is 0.30 in. In such an embodiment, the ratio of the inner diameter of the ring to the inner diameter of the chamber is about 0.9. Preferably, the ratio of the inner diameter of the ring to the inner diameter of the chamber is about 0.9 or less.

The device of the present invention can also be optimized for varying dosage ranges. One way to do so is to vary the dimensions of chamber 210 to accommodate varying sizes of capsules. For example, a chamber having an inner diameter X of 0.33 in., inner diameter Y of 0.30 in., and distance Z of 0.57 in. can be used with size 2 and size 00 capsules. It should be readily apparent to one skilled in the art that chamber 210 can be scaled to accommodate varying capsule sizes, and to accommodate those capsule sizes at varying flow rates.

The device of the present invention can be used with varying dosage ranges. A highly dispersible powder was prepared and loaded into capsules to obtain a large pre-metered dose (50 mg) and a smaller pre-metered dose (6 mg). The particle size characteristics of the powder were as follows: Dg=10.6 µm; ρ=0.11 g/cc; and Da=3.5 µm, where Dg is the mean geometric diameter, ρ is the powder density, and Da is the mean aerodynamic diameter. The aerodynamic particle size distributions were characterized using a multi-stage liquid impinger that extracted air at 60 L/min after actuating the inhaler device (D). As shown in FIG. 12, the mass fraction was measured at D, the induction port (IP) of the impactor, stages S1–S4, and the filter cutoff (SF). Size 2 capsules were used for the 6 mg dose and size 000 capsules were used for the 50 mg dose. FIG. 12 shows the results comparing the two particle size distributions obtained for the 6 mg (left bar) and 50 mg (right bar) doses. "ED" used on the graph refers to emitted dose, and FPM used on the graph refers to fine particle mass (estimate of the mass that would deposit in the lungs). The fine particle fraction <6.8 µm relative to the total dose ($FPF_{TD}$<6.8 µm) for the 6 and 50 mg doses were 74.4% and 75.0%, respectively. Similar aerodynamic particle size distributions were obtained for both doses.

FIG. 13 is a graph showing glucose (mg/dL) in beagle dogs after administration of human insulin using an aerosol generator and a device of the present invention with the low ring configuration substantially as shown in FIG. 4. The generator is a device with proven ability for forming a respirable aerosol that results in deposition of powder in dog lungs. Metered powder is presented to a chamber where the powder is dispersed by a high velocity jet of air. The dispersed powder is directed toward a baffle to separate large agglomerates before inhalation by the dog. The pharmakodynamic profile shown in FIG. 13 confirms that the device of the present invention produces a pattern of powder deposition similar to the aerosol generator.

The dogs were anesthetized for the dosing procedure. A forced maneuver was used with dogs being ventilated at 75% of their vital capacity (approximately 100 cc/s or 6 L/min for a duration of 1 second). A 4 second breath-hold was applied at the end of each inhalation. A physically smaller device was used with the low ring configuration to facilitate administration. The device performed well at the low flow rate with the anesthetized dogs using the forced maneuver. Based on these results, such a device could be used with a sleeping person or a person having breathing problems, such as from chronic obstructive pulmonary disease (COPD).

As can be seen from the description above, the device of the present invention relies upon the breath of the user to drive the inhalation process, yet the device is configured to work successfully at low flow rates. As such, the device of the present invention has particular suitability for use with individuals who cannot breath hard, such as a child, an individual with respiratory disease, or individuals who are sleeping or in a coma.

Figure 7A:
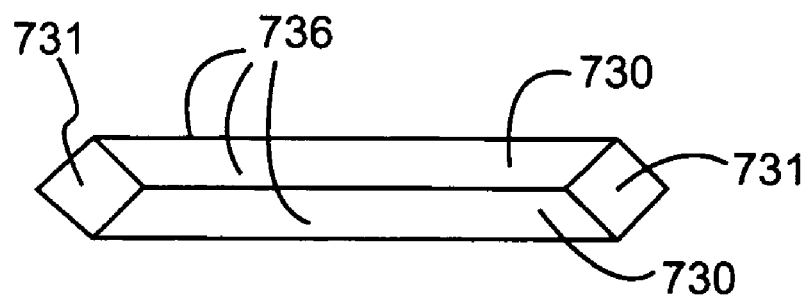
FIG. 7A is a top view of a preferred embodiment of a staple suitable for use with the device of the present invention.
Figure 7B:
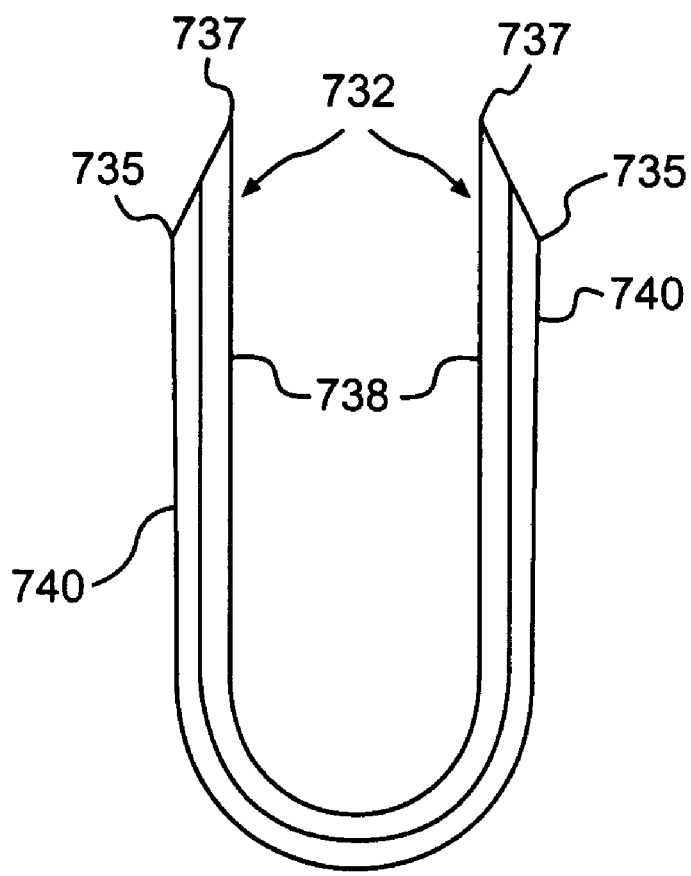
FIG. 7B is a front view of the embodiment shown in FIG. 7A.
Figure 7C:
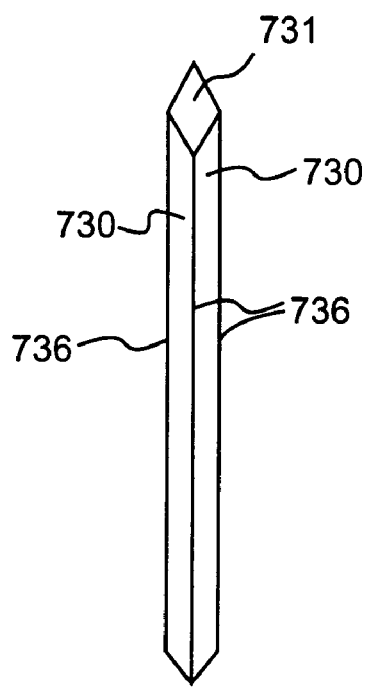
FIG. 7C is a side view of the embodiment shown in FIG. 7A.
Figure 7D:
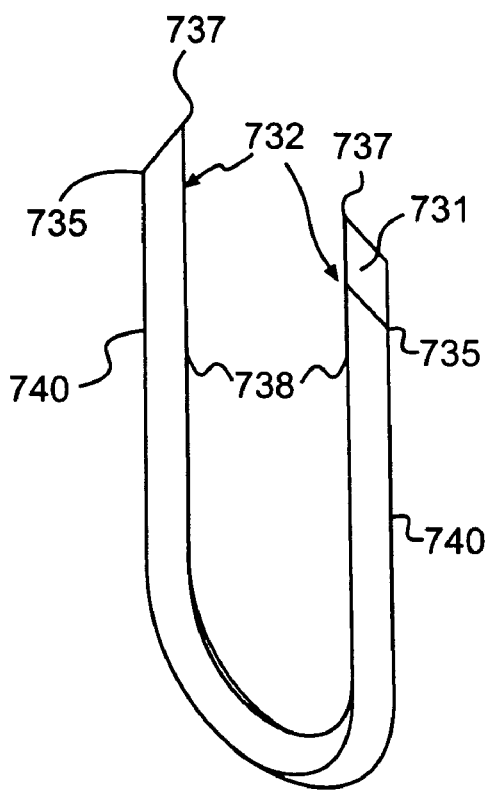
FIG. 7D is an isometric view of the embodiment shown in FIG. 7A.

Turning now to FIGS. 7A through 7D, a preferred embodiment of a staple suitable for use in the present invention is shown. The staple preferably comprises a rectangular length of material that has four planar side surfaces 730. Each planar side surface intersects with two other planar side surfaces to create a total of four non-planar edges 736. The staple is preferably bent into a substantially U-shaped configuration, thereby having a rounded portion and two prongs 732. The prongs 732 terminate at two end surfaces 731. As best seen in FIGS. 7A, 7C and 7D, end surfaces 731 are diamond-shaped.

The diamond-shaped end surfaces are created by bending the material about a non-planar edge. This configuration is best shown in FIGS. 7B and 7D. As can be seen, each prong 732 has an inner surface 738 that comprises one of the non-planar edges and an outer surface 740 that comprises the opposite non-planar edge. The inner surface 738 of each prong 732 terminates at the uppermost portion 737 of the diamond-shaped end surface, thereby creating a cutting edge for the prong. The outer surface 740 of the prong 732 terminates at the lowermost portion 735 of the diamond-shaped end surface.

FIGS. 9A and 9B depict another embodiment of a staple suitable for use in the present invention. This staple preferably comprises a rectangular length of material that has four planar side surfaces. Each planar side surface intersects with two other planar side surfaces to create a total of four non-planar edges. The staple is preferably bent into a substantially U-shaped configuration, thereby having a rounded portion and two prongs. The prongs terminate at two end surfaces that have a square shape.

The square-shaped end surfaces are created by bending the material about a planar side surface. As shown in FIG. 9A, each prong has an inner surface that comprises one of the planar side surfaces and an outer surface that comprises the opposite planar side surface. The inner surface of each prong terminates at the uppermost portion of the square-shaped end surface, thereby creating a cutting edge for the prong. The outer surface of the prong terminates at the lowermost portion of the square-shaped end surface.

FIG. 9B illustrates a puncture obtained from using the staple depicted in FIG. 9A. As shown, the holes formed by this staple have the appearance of being cut with a sharp edge. In addition, the material removed to create the hole is peeled back and remains well attached to the capsule; thereby preventing the capsule material from being inhaled by the user when the powder medicament is being dispensed.

FIG. 8 illustrates a puncture obtained from using the staple depicted in FIGS. 7A–7D. The holes formed by the staple appear to be cut with a sharp edge, and the excess material is peeled back. In testing, the effort required to puncture the capsule is lower than circular section staples, and approximately the same as a square section staple. However, during testing, no instances were noted of crushed or otherwise mispunctured capsules. These staples are extremely inexpensive to produce, approximately one-third the cost of square section staples such as those depicted in FIG. 9A.

In addition to improved puncturing performance, drug delivery from capsules punctured with the staple depicted in FIGS. 7A–7D is greatly improved. The Emitted Dose (ED) and Fine Particle Fraction (FPF) of a test powder was measured at both 20 and 60 Liters per minute (LPM). In all cases, the aerosol emitted from capsules punctured with the diamond section staple of FIGS. 7A–7D was improved over a conventional circular stock staple. Most significantly, the FPF of powder delivered at 20 liters per minute was improved almost to the level of the FPF at 60 liters per minute.

The present invention also relates to a method for dispensing powder medicaments to a user through the various embodiments of the disclosed inhalation device. In such a method, a receptacle containing the powder medicament, e.g., a capsule 219, is placed or formed into cylindrical chamber 210. When the user compresses the inhalation device, staple 230 is moved toward capsule 219 thereby puncturing capsule 219 to cause the release of powder into chamber 210. After release into the chamber, the powder is then inhaled by the user through apertures 224 and inhalation piece 226. As noted, inhalation piece 226, can be configured as either a mouth piece or a nose piece. For subsequent uses, the user merely replaces emptied capsule 219 with another capsule 219 that contains a new supply of power medicament. Alternatively, powder medicament is injected into a permanent receptacle that is formed into chamber 210.

Conclusion

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

What is claimed is:

1. A method for dispensing powder by inhalation, comprising:
    providing a powder inhalation device, the device comprising
        a first casing portion,
        a cylindrical chamber, defined by a straight wall of circular cross-section, coupled to said first casing portion, said chamber having a proximal end and a distal end and configured to receive a receptacle therein, said chamber comprising a ring circumferentially coupled to an inner surface of said chamber, wherein an inner diameter of said ring is less than an inner diameter of said chamber whereby emitted dose from said powder inhalation device is improved compared to a device with no ring, and
        a second casing portion removably coupled to said first casing portion, said second casing portion comprising an inhalation portion disposed at the proximal end of said chamber when said first and said second casing portions are coupled, said inhalation portion comprising a hemispheric region defining a plurality of apertures configured to emit powder therethrough;
    puncturing the receptacle to disperse powder in said chamber; and
    inhaling the powder through said inhalation portion.

2. The method of claim 1, wherein said inhaling step is carried out by inhaling the powder through a mouthpiece into a user's mouth.

3. The method of claim 1, wherein said inhaling step is carried out by inhaling the powder through a nose piece into a user's nose.

4. The method of claim 1, wherein said puncturing step comprises:
    moving said first and said second casing portions toward each other so that a staple disposed in the device punctures at least two holes in the receptacle.

5. The method of claim 1, wherein said puncturing step comprises:
    compressing a spring disposed in the device so that a staple disposed in the device punctures at least two holes in the receptacle.

6. The method of claim 1, wherein said puncturing step comprises:
    moving a staple disposed in the device so that said staple punctures at least two holes in the receptacle.

7. The method of claim 1, further comprising:
    inserting the receptacle into the device.

8. The method of claim 1, wherein a ratio of an inner diameter of said ring to an inner diameter of said chamber is about 0.9 or less.

9. The method of claim 8, wherein the ratio is about 0.8.

10. The method of claim 1, wherein the puncturing step is carried out using:
    a substantially U-shaped staple comprising a rounded portion and two prongs that define a non-planar inner edge and a non-planar outer edge of said staple, wherein said staple is formed from a rectangular length having two end surfaces and four planar side surfaces that intersect to form four non-planar edges, wherein said inner edge of said staple is one of said non-planar edges and said outer edge is another of said non-planar edges that is opposite said one non-planar edge, wherein each end surface is an angled diamond-shaped surface.

11. The method of claim 10, wherein each end surface has a top point at an apex of said inner edge and a bottom point at an apex of said outer edge, each top point forming a cutting point for one of said prongs.

12. The method of claim 1, wherein said ring is disposed at approximately a midpoint of said chamber.

13. The method of claim 1, wherein said ring is disposed adjacent the proximal end of said chamber.

14. A method for dispensing powder by inhalation, comprising:
    providing a powder inhalation device that comprises,
        a casing comprising at least one aperture configured to emit an emitted dose of the powder therethrough,
        a cylindrical chamber, defined by a straight wall of circular cross-section, disposed in said casing, said chamber comprising a ring circumferentially coupled to an inner surface of said chamber,
        a substantially U-shaped staple, disposed in said casing, comprising a rounded portion and two prongs that define a non-planar inner edge and a non-planar outer edge of said staple, wherein said staple is formed from a rectangular length having two end surfaces and four planar side surfaces that intersect to form four non-planar edges, wherein said inner edge of said staple is one of said non-planar edges and said outer edge is another of said non-planar edges that is opposite said one non-planar edge, wherein each end surface is an angled diamond-shaped surface;
    puncturing a receptacle containing the powder with said substantially U-shaped staple to disperse the powder in said chamber; and
    inhaling the emitted dose through said at least one aperture at a flow rate less than about 15 L/min.

15. The method of claim 14, wherein
    each end surface has a top point at an apex of said inner edge and a bottom point at an apex of said outer edge, each top point forming a cutting point for one of said prongs.

16. The method of claim 14, wherein said ring is disposed at approximately a midpoint of said chamber.

17. The method of claim 14, wherein said ring is disposed adjacent a proximal end of said chamber.

* * * * *